(12) United States Patent
Shimura

(10) Patent No.: US 6,272,198 B1
(45) Date of Patent: Aug. 7, 2001

(54) RADIATION IMAGE FORMING METHOD AND APPARATUS

(75) Inventor: Kazuo Shimura, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 09/430,299

(22) Filed: Oct. 29, 1999

(30) Foreign Application Priority Data

Oct. 29, 1998 (JP) .................................................. 10-308036

(51) Int. Cl.$^7$ ........................................................ A61B 6/03
(52) U.S. Cl. .................................................. 378/7; 378/901
(58) Field of Search ...................................... 378/4, 7, 901

(56) References Cited

U.S. PATENT DOCUMENTS

| | | | |
|---|---|---|---|
| 5,028,784 | 7/1991 | Arakawa et al. | 250/327.2 |
| 5,848,114 | 12/1998 | Kawai et al. | 378/4 |
| 6,041,097 | * 3/2000 | Roos et al. | 378/62 |

FOREIGN PATENT DOCUMENTS

| | | |
|---|---|---|
| 10-108858 | 4/1998 | (JP) . |
| 10-94538 | 4/1998 | (JP) . |

OTHER PUBLICATIONS

"Present State and Future of Cone–Beam CT Development", Image Information (M), pp. 122–127, Jan. 1988.
"Morphology" by Hidefumi Kobatake, Corona Co., First Edition, Nov. 15, 1996.
"Practical cone–beam algorithm", Feldkamp LA, Davis LC, Kress JW, J. Opt. Soc. Am. A, 1984; 1, pp. 612–619.
"Image Analysis Handbook", Publishing Circle of the University of Tokyo, pp. 356–371.

* cited by examiner

Primary Examiner—David V. Bruce
(74) Attorney, Agent, or Firm—Sughrue, Mion, Zinn, Macpeak & Seas, PLLC

(57) ABSTRACT

A plurality of radiation image signals, which represent radiation images of an object, are obtained by irradiating radiation from different directions to the object and detecting the radiation carrying image information of the object via a scattered radiation removing device for removing radiation having been scattered by the object. Image signal components representing a pattern of the scattered radiation removing device, which are contained in the radiation image signals, are reduced, and pattern-reduced radiation image signals, in which the image signal components representing the pattern of the scattered radiation removing device have been reduced, are thereby obtained. At least either one of a volume signal and a tomographic image signal representing an image of the object is then obtained from the pattern-reduced radiation image signals.

8 Claims, 1 Drawing Sheet

RADIATION IMAGE FORMING METHOD AND APPARATUS

BACKGROUND OF THE INVENTION

1. Field of the Invention

This invention relates to a radiation image forming method and apparatus for obtaining at least either one of a volume signal and a tomographic image signal representing an image of an object. This invention particularly relates to a radiation image forming method and apparatus, wherein radiation image signals representing radiation images of an object are detected via scattered radiation removing means, which removes radiation scattered by the object, and at least either one of a volume signal and a tomographic image signal representing an image of an object, is obtained from the radiation image signals.

2. Description of the Prior Art

In the fields of medical images, systems for detecting two-dimensional radiation image signals (e.g., tomographic image signals), such as computed tomography scanners (CT scanners) and magnetic resonance imaging systems (MRI systems), have heretofore been used widely. (Such systems will hereinbelow be referred to as the radiation image detecting systems for two-dimensional images.)

Also, recently, research has been conducted to detect three-dimensional radiation image signals. As techniques for detecting three-dimensional radiation image signals, for example, helical CT and cone-beam CT have been proposed. (Such techniques are described in, for example, "Present State and Future of Cone-Beam CT Development," Image Information (M), pp. 122–127, January 1988; and Japanese Unexamined Patent Publication No. 9(1997)-253079.)

With the cone-beam CT, a radiation source and a two-dimensional radiation detector are rotated around an object, radiation is irradiated from the radiation source to the object, and a three-dimensional radiation image signal (i.e., a volume signal) representing the object image is acquired from radiation image signals (projected image signals), which have been detected at respective positions of rotation by the radiation detector. The systems for detecting three-dimensional radiation image signals will hereinbelow be referred to as the radiation image detecting systems for three-dimensional images. Also, the aforesaid radiation image detecting systems for two-dimensional images and the radiation image detecting systems for three-dimensional images will hereinbelow be referred to simply as the radiation image detecting systems.

In the radiation image detecting systems described above, such that radiation scattered by an object may not be detected, a grid comprising a material impermeable to radiation, such as lead, and a material permeable to radiation, such as aluminum or wood, which are arrayed alternately at a small pitch of, e.g., 4.0 pieces/mm, is often located between the object and radiation detecting means, and image recording operation is performed in this state. The utilization of the grid is advantageous in that radiation scattered by the object does not impinge upon the radiation detecting means, and therefore radiation image signals with high contrast can be obtained.

However, in cases where an image recording operation is performed by utilizing the grid, a stripe-like grid pattern is detected together with the object image by the radiation detecting means. In the radiation image detecting systems described above, the volume signal or the tomographic image signal is obtained from the radiation image signals, which have been detected by the radiation detecting means. Therefore, in such cases, the volume signal or the tomographic image signal is obtained from the radiation image signals carrying the information of the object image and the grid pattern. As a result, an artifact due to the grid pattern occurs in the reconstructed three-dimensional image or the reconstructed tomographic image. Accordingly, the problems occur in that a correct image cannot be reconstructed, and an image, which has good image quality and can serve as an effective tool in, particularly, the efficient and accurate diagnosis of an illness, cannot be obtained.

SUMMARY OF THE INVENTION

The primary object of the present invention is to provide a radiation image forming method for use in a radiation image detecting system, wherein at least either one of a volume signal and a tomographic image signal representing an image of an object is obtained from radiation image signals, which represent radiation images of the object and which have been detected via scattered radiation removing means, such as a grid, such that an artifact due to a pattern of the scattered radiation removing means may not occur in an image reproduced from the volume signal or the tomographic image signal.

Another object of the present invention is to provide an apparatus for carrying out the radiation image forming method.

The present invention provides a radiation image forming method, wherein at least either one of a volume signal and a tomographic image signal representing an image of an object is obtained from a plurality of radiation image signals, which represent radiation images of the object and which have been obtained by irradiating radiation from different directions to the object and detecting the radiation carrying image information of the object via scattered radiation removing means for removing radiation having been scattered by the object, the method comprising the steps of:

i) reducing image signal components representing a pattern of the scattered radiation removing means, which are contained in the radiation image signals, pattern-reduced radiation image signals, in which the image signal components representing the pattern of the scattered radiation removing means have been reduced, being thereby obtained, and ii) obtaining at least either one of the volume signal and the tomographic image signal from the pattern-reduced radiation image signals.

The scattered radiation removing means acts to prevent the radiation, which has been scattered by the object, from impinging upon radiation detecting means. By way of example, the scattered radiation removing means may be a grid or a collimator for removing scattered radiation, which is employed in an ordinary X-ray image recording operation. The collimator is constituted of partitions, which are arrayed at predetermined intervals. The partitions absorb the scattered radiation, which travels in oblique directions due to the scattering, and transmit only the primary radiation, which travels straightly toward the object. The grid has basically the same structure as the structure of the collimator. In this specification, the scattered radiation removing means constituted of the partitions arrayed at large intervals (of, e.g., at least 1 mm) is referred to as the collimator, and the scattered radiation removing means constituted of the partitions arrayed at small intervals is referred to as the grid.

The reducing of the image signal components representing the pattern of the scattered radiation removing means, which are contained in the radiation image signals, may be performed by utilizing one of various techniques. For example, the pattern of the scattered radiation removing means is superposed as a linear pattern upon the image represented by the image signal, which is detected by the radiation detecting means. Therefore, one of various techniques for reducing the linear pattern may be employed. Specifically, a technique for performing spatial-domain filtering processing, frequency-domain filtering processing, morphology filtering processing, or the like, may be employed. With the spatial-domain filtering processing, frequency components of the image signal corresponding to the frequency of the linear pattern are reduced by utilizing a spatial-domain filter. (The spatial-domain filtering processing is described in, for example, Japanese Unexamined Patent Publication Nos. 3(1991)-114039 and 3(1991)-12785.) With the frequency-domain filtering processing, the image signal is transformed into the frequency domain with Fourier transform, or the like, frequency components corresponding to the frequency of the linear pattern are reduced, and thereafter inverse transform is performed. (The frequency-domain filtering processing is described in, for example, Japanese Unexamined Patent Publication No. 3(1991)-12785.) With the morphology filtering processing, the linear pattern contained in the image is reduced by performing a morphology operation, such as opening processing. In particular, the morphology filtering processing is efficient for an image, in which the intervals of the linear pattern are larger than the width of each line of the linear pattern as in the cases of the collimator described above. (The morphology filtering processing is described in, for example, "Morphology" by Hidefumi Kobatake, Corona Co., First Edition, Nov. 15, 1996, and Japanese Unexamined Patent Publication Nos. 10(1998)-94538 and 10(1998)-108858.)

The present invention also provides an apparatus for carrying out the radiation image forming method in accordance with the present invention. Specifically, the present invention also provides a radiation image forming apparatus comprising image signal forming means for obtaining at least either one of a volume signal and a tomographic image signal representing an image of an object from a plurality of radiation image signals, which represent radiation images of the object and which have been obtained by irradiating radiation from different directions to the object and detecting the radiation carrying image information of the object via scattered radiation removing means for removing radiation having been scattered by the object, wherein the apparatus further comprises pattern reducing means for reducing image signal components representing a pattern of the scattered radiation removing means, which are contained in the radiation image signals, pattern-reduced radiation image signals, in which the image signal components representing the pattern of the scattered radiation removing means have been reduced, being thereby obtained, and the image signal forming means obtains at least either one of the volume signal and the tomographic image signal from the pattern-reduced radiation image signals, which have been obtained from the pattern reducing means.

With the radiation image forming method and apparatus in accordance with the present invention, the image signal components representing the pattern of the scattered radiation removing means, which are contained in the radiation image signals, are reduced. Also, at least either one of the volume signal and the tomographic image signal is obtained from the pattern-reduced radiation image signals, in which the image signal components representing the pattern of the scattered radiation removing means have been reduced. Therefore, an artifact due to the pattern of a grid, or the like, does not occur in the reconstructed three-dimensional image or the reconstructed tomographic image. Accordingly, an image appropriate for use in making a diagnosis, or the like, can be reconstructed.

DESCRIPTION OF THE PREFERRED EMBODIMENTS

Figure 1:
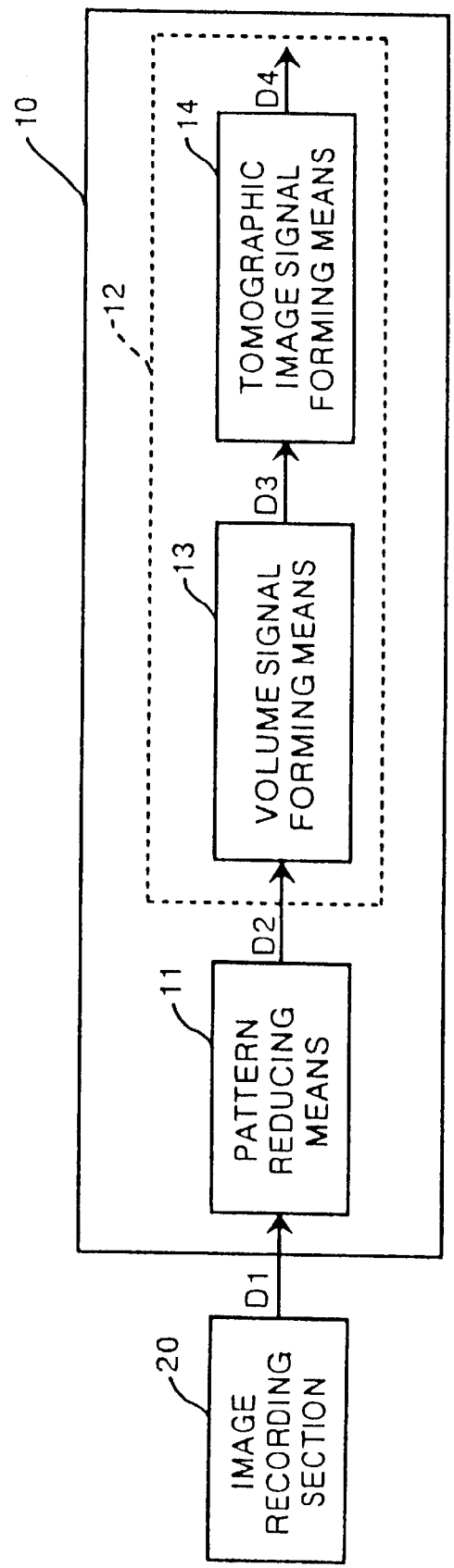
FIG. 1 is a block diagram showing an embodiment of the radiation image forming apparatus in accordance with the present invention.

The present invention will hereinbelow be described in further detail with reference to the accompanying drawing.

FIG. 1 is a block diagram showing an embodiment of the radiation image forming apparatus in accordance with the present invention. With reference to FIG. 1, a radiation image forming apparatus 10 is designed for use in a radiation image detecting system for three-dimensional images, with which three-dimensional radiation image signals are detected. The radiation image forming apparatus 10 comprises pattern reducing means 11 for reducing image signal components representing a pattern of scattered radiation removing means, which are contained in received radiation image signals D1. Pattern-reduced radiation image signals D2, in which the image signal components representing the pattern of the scattered radiation removing means have been reduced, are obtained from the pattern reducing means 11. The radiation image forming apparatus 10 also comprises image signal forming means 12 for obtaining a volume signal D3 and a tomographic image signal D4. The radiation image forming apparatus 10 further comprises storage means (not shown) for storing the received radiation image signals D1, the volume signal D3, and the tomographic image signal D4.

The image signal forming means 12 comprises volume signal forming means 13 for obtaining the volume signal D3, which represents a three-dimensional image of an object, from the pattern-reduced radiation image signals D2 received from the pattern reducing means 11. The image signal forming means 12 also comprises tomographic image signal forming means 14 for obtaining the tomographic image signal D4, which represents a tomographic image of a predetermined tomographic layer in the object, from the volume signal D3.

The volume signal forming means 13 may utilize one of various known calculation techniques for reconstructing three-dimensional image signals. For example, in cases where the radiation image forming apparatus 10 is to be utilized for cone-beam CT, the volume signal forming means 13 may utilize a Feldkamp algorithm, or the like. (The Feldkamp algorithm is described in "Practical Cone-Beam Algorithm" by Feldkamp L A, Davis L C, and Kress J W, J. Opt. Soc. Am. A, 1984;1, pp. 612–619.)

The tomographic image signal forming means 14 may be designed to form the tomographic image signal D4, which represents a tomographic image, such as a sagittal section image (a median section image) of a predetermined tomographic layer in the object, a rendering image of the predetermined tomographic layer, or the like.

The radiation image forming apparatus 10 is connected to an image recording section 20. In the image recording section 20, radiation is irradiated from different directions to the object, and the radiation carrying the image information of the object is detected via scattered radiation removing means (not shown), such as a grid or a collimator, for removing radiation having been scattered by the object. A plurality of the radiation image signals D1, which represent radiation images of the object, are detected in the image recording section 20. The radiation image signals D1 are fed into the radiation image forming apparatus 10.

The pattern reducing means 11 may utilize one of various techniques for reducing the image signal components representing the pattern of the scattered radiation removing means, which are contained in the radiation image signals D1. For example, the pattern reducing means 11 may utilize the technique for performing the spatial-domain filtering processing, the frequency-domain filtering processing, or the morphology filtering processing, which are described above.

How the radiation image forming apparatus 10 operates will be described hereinbelow.

Firstly, in the image recording section 20, radiation is produced by a radiation source and irradiated from a predetermined direction of projection to the object. The radiation carrying the image information of the object is detected via the scattered radiation removing means. Specifically, the radiation carrying the image information of the object is passed through the scattered radiation removing means, and only the radiation having passed through the scattered radiation removing means is detected by radiation detecting means. In this manner, a radiation image signal D1, which represents a radiation image of the object, is detected. The thus detected radiation image signal D1 is stored in the storage means (not shown). Thereafter, the radiation source and the radiation detecting means are rotated by a predetermined angle around the object, and a radiation image signal D1 at the position of rotation (or the direction of projection) is obtained in the same manner as that described above. The thus detected radiation image signal D1 is stored in the storage means (not shown). The operation described above is repeated, and a plurality of the radiation image signals D1 are detected with respect to various different positions of rotation.

Thereafter, the pattern reducing means 11 reads the radiation image signals D1 from the storage means (not shown) and reduces the image signal components representing the pattern of the scattered radiation removing means, which are contained in the radiation image signals D1. In cases where the pattern reducing means 11 utilizes the technique for performing the spatial-domain filtering processing, the frequency components corresponding to the frequency of the linear pattern of the scattered radiation removing means, which are contained in the radiation image signals D1, are reduced by utilizing a spatial-domain filter, and the pattern-reduced radiation image signals D2 are thereby obtained. (The spatial-domain filtering processing is described in, for example, Japanese Unexamined Patent Publication Nos. 3(1991)-114039 and 3(1991)-12785.) In cases where the pattern reducing means 11 utilizes the technique for performing the frequency-domain filtering processing, each of the radiation image signals D1 is transformed into the frequency domain with Fourier transform, or the like, and the frequency components corresponding to the frequency of the linear pattern of the scattered radiation removing means are reduced. Thereafter, inverse transform is performed, and each of the pattern-reduced radiation image signals D2 is thereby obtained. (The frequency-domain filtering processing is described in, for example, Japanese Unexamined Patent Publication No. 3(1991)-12785.) In cases where the pattern reducing means 11 utilizes the technique for performing the morphology filtering processing, the image signal components representing the linear pattern of the scattered radiation removing means are reduced by performing a morphology operation, such as opening processing, and the pattern-reduced radiation image signals D2 are thereby obtained. (The morphology filtering processing is described in, for example, "Morphology" by Hidefumi Kobatake, Corona Co., First Edition, Nov. 15, 1996, and Japanese Unexamined Patent Publication Nos. 10(1998)-94538 and 10(1998)-108858.)

The pattern-reduced radiation image signals D2, in which the image signal components representing the pattern of the scattered radiation removing means have been reduced, are stored in the storage means. In this specification, detailed explanation of the spatial-domain filtering processing, the frequency-domain filtering processing, and the morphology filtering processing is omitted.

The volume signal forming means 13 forms the volume signal D3, which represents the image of the object, from the pattern-reduced radiation image signals D2 having been read from the storage means. The obtained volume signal D3 is stored in the storage means. In order for the volume signal D3 to be formed, one of various known calculation techniques for reconstructing three-dimensional image signals, such as the Feldkamp algorithm described above, may be employed. In this specification, detailed explanation of how the volume signal D3 is calculated is omitted.

In accordance with the volume signal D3 having been read from the storage means, the tomographic image signal forming means 14 forms the tomographic image signal D4, which represents a tomographic image, such as a sagittal section image (a median section image) of a predetermined tomographic layer in the object, a rendering image of the predetermined tomographic layer, or the like.

When necessary, the volume signal D3 or the tomographic image signal D4 is transformed into an image signal to be used for reproducing a visible image. The transformed image signal is fed into an image display device (not shown), and the three-dimensional image or the tomographic image represented by the corresponding image signal is reproduced as a visible image on the image display device.

As described above, with this embodiment of the radiation image forming apparatus in accordance with the present invention, the image signal components representing the pattern of the scattered radiation removing means, which are contained in the radiation image signals D1, are reduced, and the pattern-reduced radiation image signals D2, in which the image signal components representing the pattern of the scattered radiation removing means have been reduced, are thereby obtained. Thereafter, the volume signal D3 is formed from the pattern-reduced radiation image signals D2. Also, the tomographic image signal D4 is formed from the volume signal D3. Therefore, an artifact due to the pattern of the grid, or the like, does not occur in the reconstructed three-dimensional image and the reconstructed tomographic image. Accordingly, a three-dimensional image and a tomographic image appropriate for use in making a diagnosis, or the like, can be reproduced and displayed on the image display device.

In the embodiment described above, the radiation image forming apparatus in accordance with the present invention is designed for use in the radiation image detecting system for three-dimensional images. However, the radiation image forming apparatus in accordance with the present invention is not limited to the use in the radiation image detecting system for three-dimensional images and may be designed for use in a radiation image detecting system for two-dimensional images. In such cases, the volume signal forming means 13 employed in the aforesaid embodiment may be replaced by, for example, image signal reconstructing means utilizing a filter compensation inverse projection technique. (The filter compensation inverse projection technique is described in, for example, Image Analysis Handbook, Publishing Circle of the University of Tokyo, pp. 356–371.)

What is claimed is:

1. A radiation image forming method, wherein at least either one of a volume signal and a tomographic image signal representing an image of an object is obtained from a plurality of radiation image signals, which represent radiation images of the object and which have been obtained by irradiating radiation from different directions to the object and detecting the radiation carrying image information of the object via scattered radiation removing means for removing radiation having been scattered by the object, the method comprising the steps of:

i) reducing image signal components representing a pattern of the scattered radiation removing means, which are contained in the radiation image signals, pattern-reduced radiation image signals, in which the image signal components representing the pattern of the scattered radiation removing means have been reduced, being thereby obtained, and ii) obtaining at least either one of the volume signal and the tomographic image signal from said pattern-reduced radiation image signals.

2. A method as defined in claim 1 wherein the reducing of the image signal components representing the pattern of the scattered radiation removing means, which are contained in the radiation image signals, is performed by utilizing spatial-domain filtering processing.

3. A method as defined in claim 1 wherein the reducing of the image signal components representing the pattern of the scattered radiation removing means, which are contained in the radiation image signals, is performed by utilizing frequency-domain filtering processing.

4. A method as defined in claim 1 wherein the reducing of the image signal components representing the pattern of the scattered radiation removing means, which are contained in the radiation image signals, is performed by utilizing morphology filtering processing.

5. A radiation image forming apparatus comprising image signal forming means for obtaining at least either one of a volume signal and a tomographic image signal representing an image of an object from a plurality of radiation image signals, which represent radiation images of the object and which have been obtained by irradiating radiation from different directions to the object and detecting the radiation carrying image information of the object via scattered radiation removing means for removing radiation having been scattered by the object, wherein the apparatus further comprises pattern reducing means for reducing image signal components representing a pattern of the scattered radiation removing means, which are contained in the radiation image signals, pattern-reduced radiation image signals, in which the image signal components representing the pattern of the scattered radiation removing means have been reduced, being thereby obtained, and the image signal forming means obtains at least either one of the volume signal and the tomographic image signal from said pattern-reduced radiation image signals, which have been obtained from said pattern reducing means.

6. An apparatus as defined in claim 5 wherein said pattern reducing means performs the reducing of the image signal components representing the pattern of the scattered radiation removing means, which are contained in the radiation image signals, by utilizing spatial-domain filtering processing.

7. An apparatus as defined in claim 5 wherein said pattern reducing means performs the reducing of the image signal components representing the pattern of the scattered radiation removing means, which are contained in the radiation image signals, by utilizing frequency-domain filtering processing.

8. An apparatus as defined in claim 5 wherein said pattern reducing means performs the reducing of the image signal components representing the pattern of the scattered radiation removing means, which are contained in the radiation image signals, by utilizing morphology filtering processing.

* * * * *